United States Patent
Schwarz et al.

(10) Patent No.: US 12,053,419 B2
(45) Date of Patent: Aug. 6, 2024

(54) EYE MASK WITH MOVABLE SPEAKERS

(71) Applicant: MANTA SLEEP LLC., Jackson, WY (US)

(72) Inventors: Benjamin Schwarz, Jackson, WY (US); Mark Zhang, Jackson, WY (US)

(73) Assignee: Manta Sleep LLC, Jackson, WY (US)

( * ) Notice: Subject to any disclaimer, the term of this patent is extended or adjusted under 35 U.S.C. 154(b) by 57 days.

(21) Appl. No.: 17/969,312

(22) Filed: Oct. 19, 2022

(65) Prior Publication Data

US 2024/0130894 A1    Apr. 25, 2024

(51) Int. Cl.
*A61F 9/04* (2006.01)
*A41D 23/00* (2006.01)

(52) U.S. Cl.
CPC ..................... *A61F 9/04* (2013.01)

(58) Field of Classification Search
CPC ..................................... A61F 9/04
See application file for complete search history.

(56) References Cited

U.S. PATENT DOCUMENTS

| | | | | |
|---|---|---|---|---|
| 5,273,243 | A * | 12/1993 | Abdallah | B60R 11/0217 181/150 |
| 5,886,739 | A * | 3/1999 | Winningstad | H04N 7/185 348/115 |
| 8,121,329 | B2 * | 2/2012 | Groset | H04R 5/02 381/334 |
| 8,213,670 | B2 | 7/2012 | Lai | |
| 10,575,080 | B2 * | 2/2020 | Dowding-Young | H04R 1/1041 |
| 10,646,377 | B2 * | 5/2020 | Schwarz | A61F 9/045 |
| 11,207,490 | B1 | 12/2021 | Fried | |
| 11,223,915 | B2 * | 1/2022 | McKinney | H04R 25/604 |
| 2009/0180660 | A1 * | 7/2009 | Groset | H04R 5/02 381/386 |
| 2015/0092972 | A1 | 4/2015 | Lai et al. | |
| 2017/0264994 | A1 | 9/2017 | Gordon et al. | |
| 2019/0110927 | A1 * | 4/2019 | Schwarz | A61F 9/04 |
| 2019/0149903 | A1 * | 5/2019 | Dowding-Young | A61F 9/04 381/74 |
| 2022/0007965 | A1 * | 1/2022 | Tiron | A61B 5/6898 |
| 2023/0190140 | A1 * | 6/2023 | Tiron | A61B 5/746 600/534 |

FOREIGN PATENT DOCUMENTS

| | | |
|---|---|---|
| CN | 204272343 U | 4/2015 |
| CN | 207666768 U | 7/2018 |
| WO | 2018081834 A1 | 5/2018 |

* cited by examiner

*Primary Examiner* — Robert H Muromoto, Jr.
(74) *Attorney, Agent, or Firm* — Rosenberg, Klein & Lee (57) ABSTRACT

An eye mask with movable speakers is provided. The eye mask has a mask main body and two speaker assemblies. The mask main body is configured to cover a user's eyes and ears and comprises two inner spaces. The two inner spaces correspond to the user's ears in location. The two speaker assemblies are mounted in the inner spaces respectively, and at least one of the speaker assemblies is capable of moving in the corresponding inner space. When wearing the present eye mask, the user may cover eyes first and then connect and tie two ends of the mask main body, thereby securing the eye mask on the head. In the meantime, the mask also covers the user's ears. Then, the two speaker assemblies may be moved in the inner spaces to align with the user's ears respectively.

9 Claims, 8 Drawing Sheets

EYE MASK WITH MOVABLE SPEAKERS

BACKGROUND OF THE PRESENT DISCLOSURE

1. Field of the Present Disclosure

The present disclosure relates to an article for daily use, especially to an eye mask that shades light.

2. Description of the Prior Arts

An eye mask is a daily necessity for helping people to sleep. If the brightness of the environment is high, it will easily affect the sleep quality and even make many people struggle to fall asleep. Therefore, an eye mask worn during sleep for shading light from the environment becomes an important apparatus to maintain the sleep quality. Besides, noise in the environment also bothers people during sleep. Thus, many people like to sleep with music or white noise, which blocks the noise from the environment and provides another way to help them fall asleep.

As a result, some eye masks include two speakers to cover the user's ears. Because the structure of the eye mask is fixed but the head size differs from person to person, the speakers may not exactly over the ears. Thus, the environment noise is still capable of entering the user's ears. Accordingly, a need remains for improved sleep masks having speaker and audio functionality.

SUMMARY OF THE PRESENT DISCLOSURE

The present disclosure provides for an eye mask with one or more movable speakers configured for noise blocking or canceling in addition to shading light.

In an example, the eye mask with movable speakers includes a mask main body and two speaker assemblies, the two speaker assemblies are spaced apart on opposite ends of the mask main body and configured to engage with ears of a user. The mask main body is configured to cover a user's eyes and ears and defines two inner spaces. The two inner spaces may generally correspond to the user's ears in location. The two speaker assemblies are provided in the inner spaces respectively, and at least one of the speaker assemblies is configured for moving in the corresponding inner space such that the speakers may align or be near the user's ears.

During use, a user may cover their eyes or secure the mask around their head and then connect and/or tie two ends of the mask main body, thereby securing the eye mask on the head. The mask is configured to also cover the user's ears. Then, the two speaker assemblies may be adjusted or moved within the inner spaces so that the two speaker assemblies can align or be near the user's ears respectively. As a result, for example, the two speaker assemblies can provide any desired sound, like music or white noise to the user's ears, which can be configured to sufficiently block any surrounding or environment noise and helps the user to sleep.

Other objectives, advantages and novel features of the present disclosure will become more apparent from the following detailed description when taken in conjunction with the accompanying drawings.

DETAILED DESCRIPTION OF THE PREFERRED EMBODIMENTS

Figure 1:
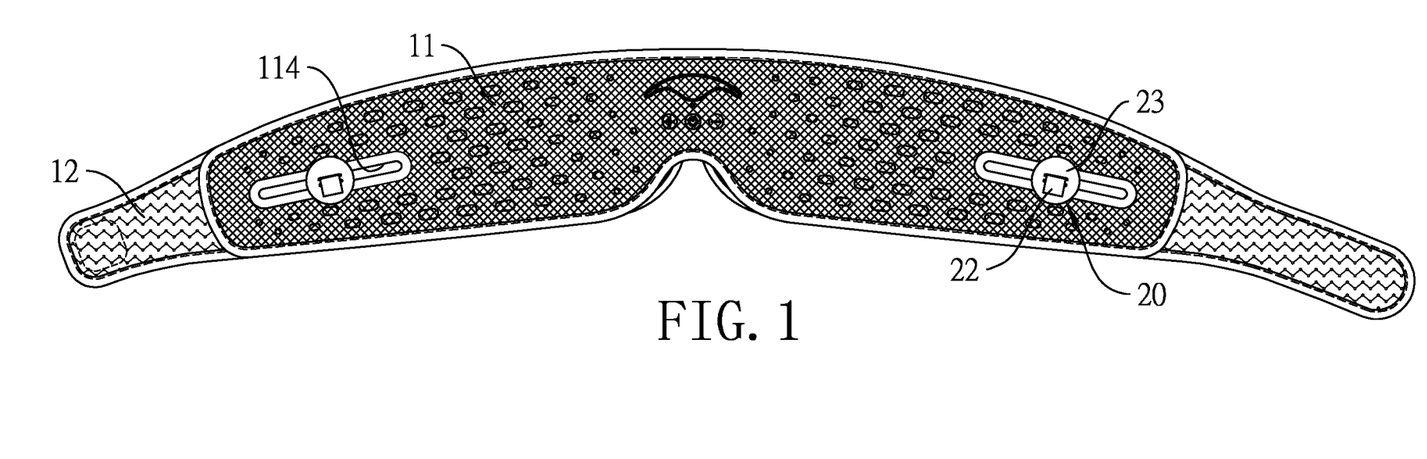
FIG. 1 is a front view of an eye mask with movable speakers in accordance with the present disclosure.
Figure 2:
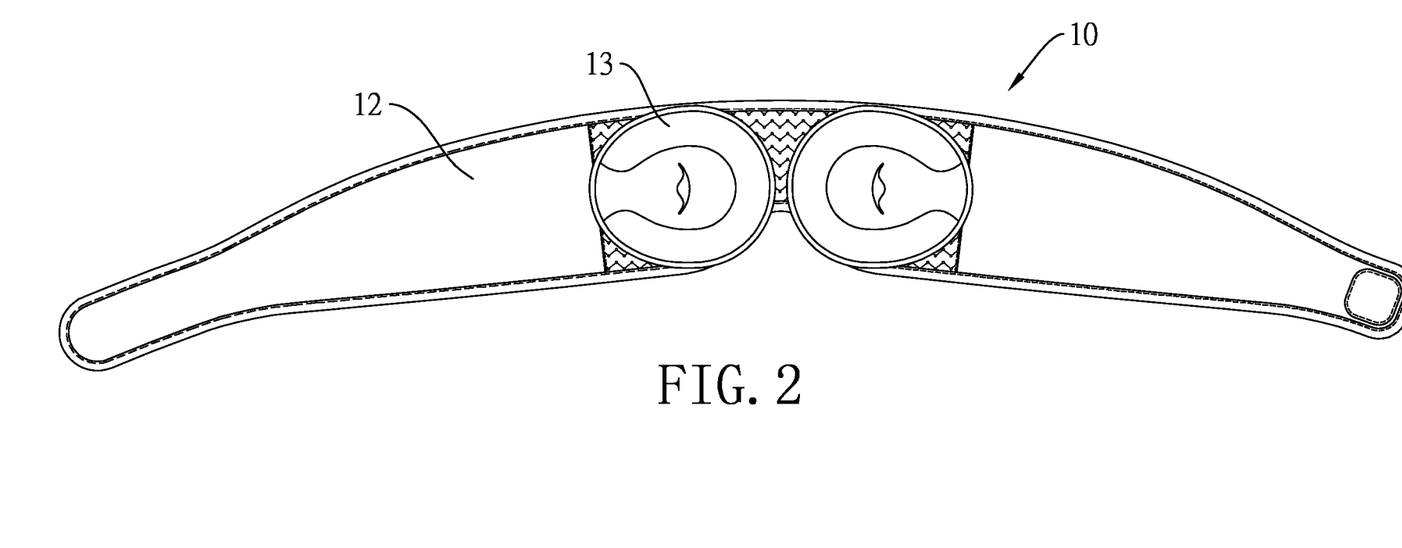
FIG. 2 is a rear view of the eye mask in FIG. 1.
Figure 3:
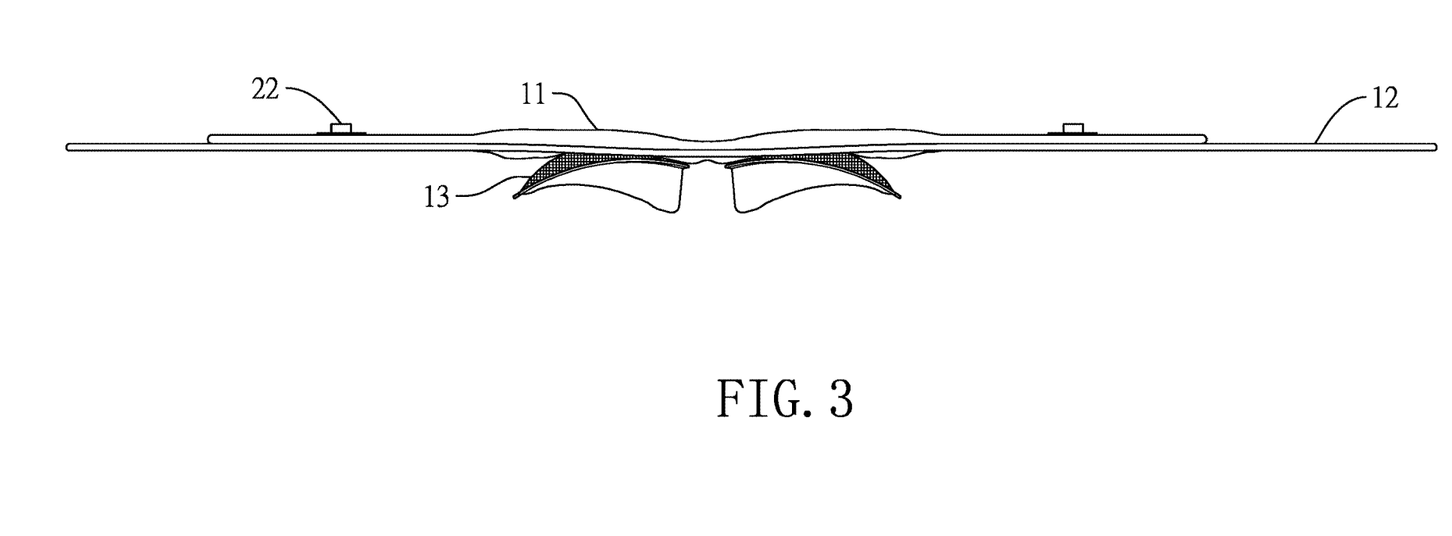
FIG. 3 is a top view of the eye mask in FIG. 1.

Please refer to FIG. 1 to FIG. 3. An eye mask is provided in accordance with the present disclosure includes a mask main body 10 and two speaker assemblies 20.

The mask main body 10 is configured to cover a user's eyes and ears and thereby shades light. The mask main body 10 may only include one headband, such that said headband in use is configured to cover the user's eyes and ears and receive the two speaker assemblies 20. The mask main body 10 may include two headbands configured to compliment and engage with each other via a reusable adhesive. In this example, the main body 10 includes a first headband 11 and a second headband 12. The first headband 11 is configured to receive the two speaker assemblies 20, and the second headband 12 is configured to cover a user's eyes and ears. In this embodiment, the mask main body 10 further includes two eye cups 13. The two eye cups 13 are configured to fit contours of eye sockets and cover the user's eyes, and thereby the eye cups 13 shade light thoroughly and provide better wearing experience. Eye cups 13 include a comfort pad that substantially surrounds an eye socket and defines an open pocket that provides space for a user's eye. This pocket configuration makes blinking and resting more comfortable as the surface of the eye cup generally avoids direct contact with the user's eyelid and/or eyelashes.

Figure 4:
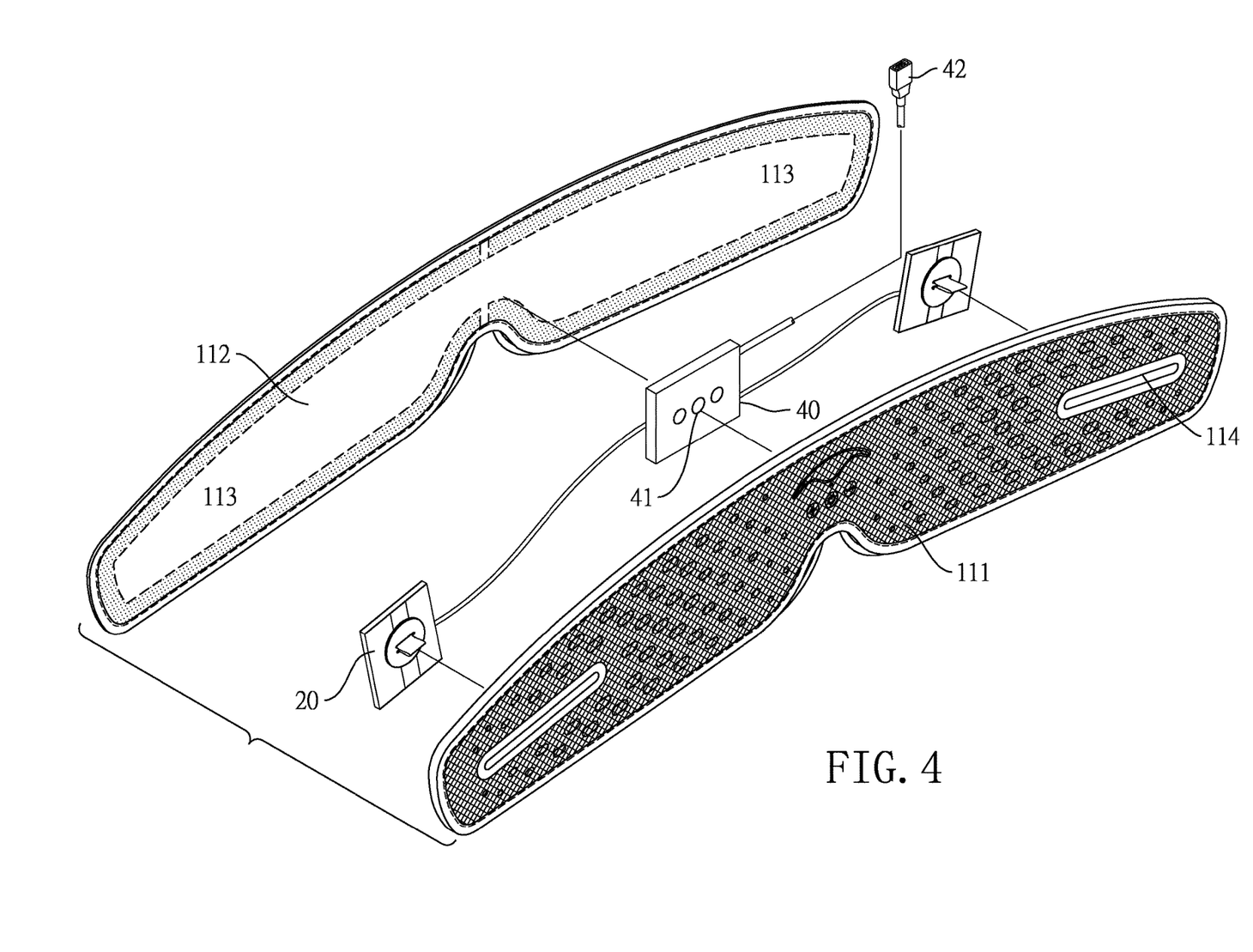
FIG. 4 is an exploded view of a first headband of the eye mask in FIG. 1.
Figure 5:
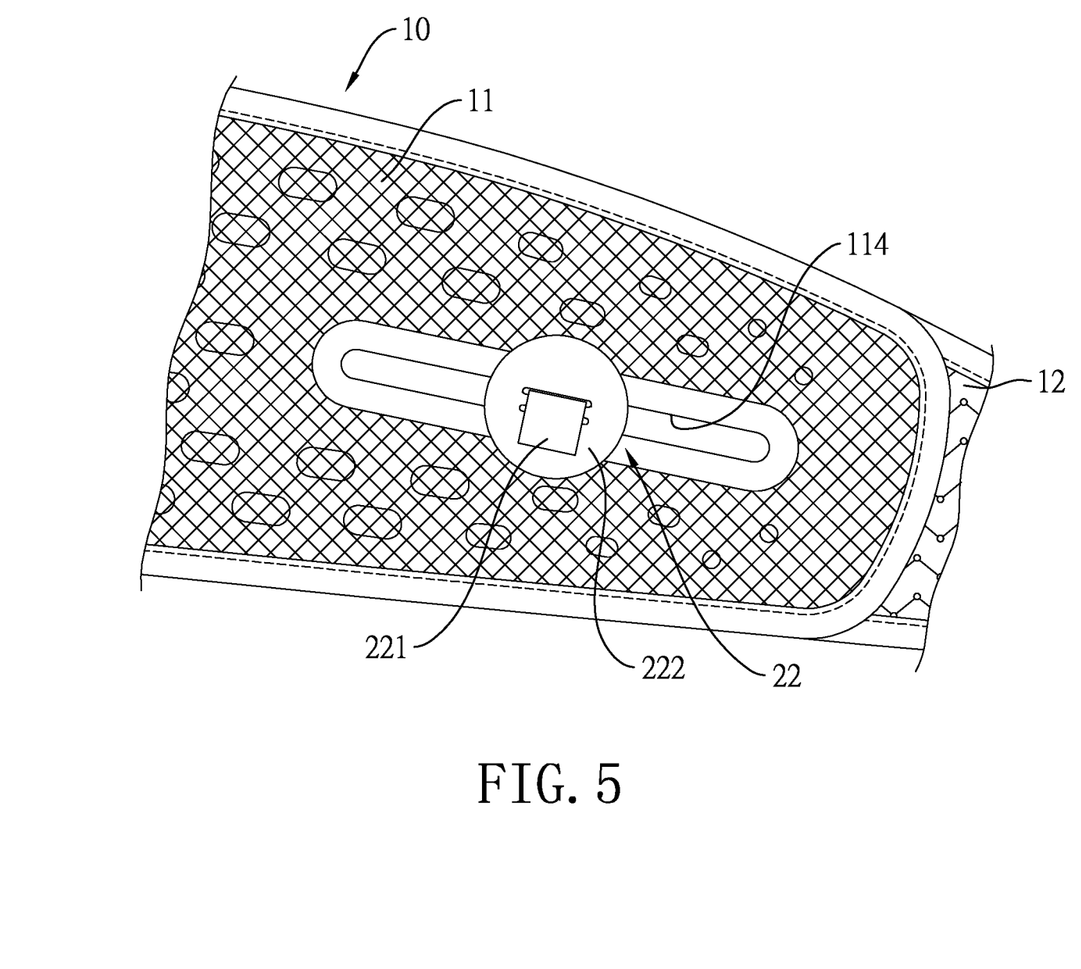
FIG. 5 is an enlarged view of a slot and a speaker assembly of the eye mask in FIG. 1.

Please refer to FIG. 4 and FIG. 5. In this embodiment, the first headband 11 includes a first sheet 111 and a second sheet 112, and defines at least two inner spaces 113 formed between the first sheet 111 and the second sheet 112 and at least one slot 114 formed on the first sheet 111. The two inner spaces 113 correspond to the user's ears in location and form pockets or cavities for receiving a speaker assembly 20. The at least one slot 114 is formed to allow access to at least one the inner spaces 113. In this embodiment, the first headband 11 defines two slots 114 and each slot 114 allows access to a corresponding inner spaces 113. In this example, each slot 114 extends horizontally along a horizontal axis generally defined by the sleep mask when fully extended. This defines a length of the slot 114 and a width W1 is defined perpendicular to the axis of the length of the slot 114. The width W1 of each slot 114 is sized and shaped to be smaller than a width defined by the corresponding inner space 113.

Figure 6:
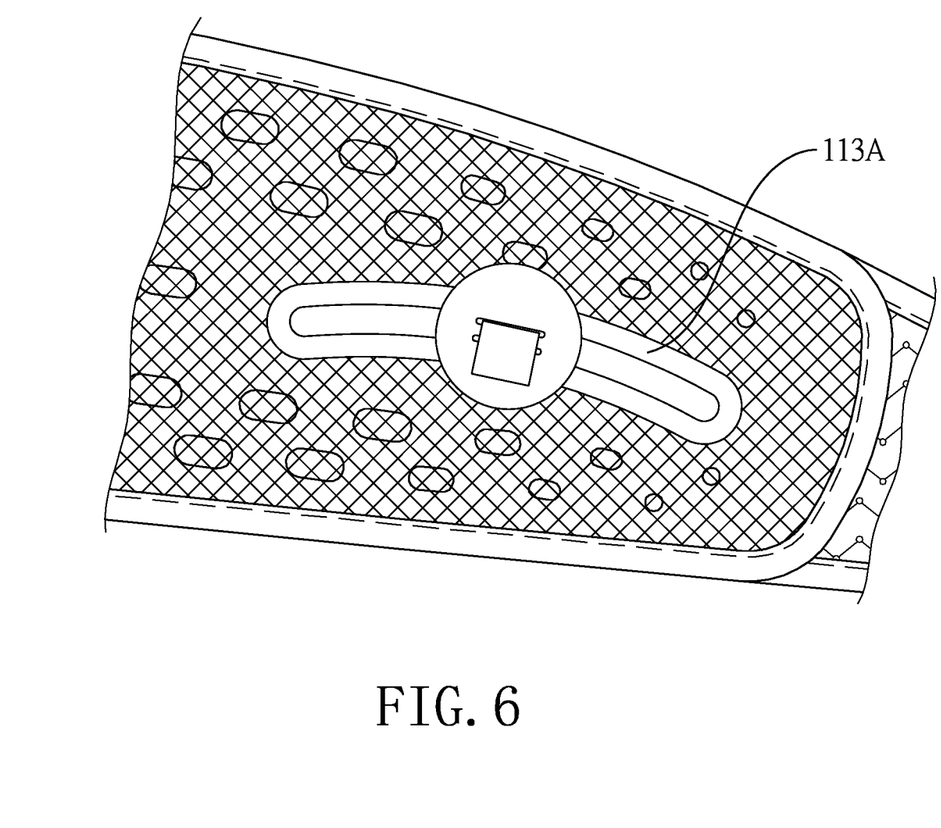
FIG. 6 is an enlarged view of a slot of the eye mask in another configuration of the present disclosure.
Figure 7:
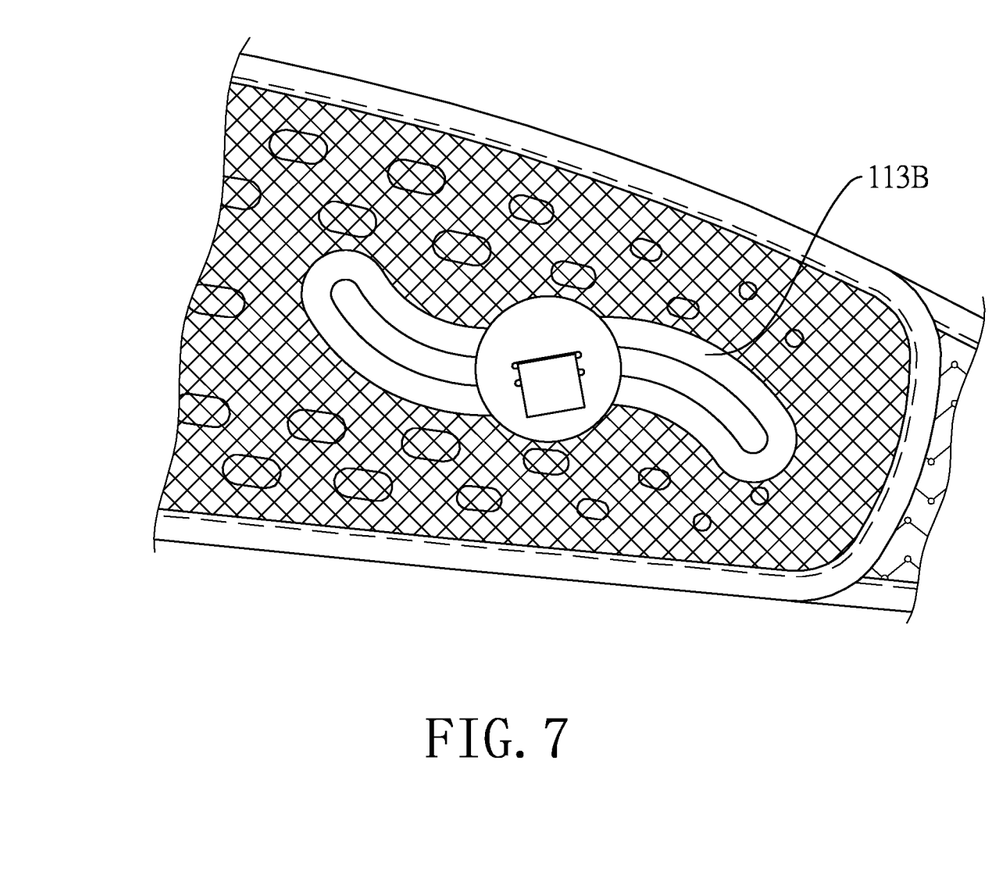
FIG. 7 is an enlarged view of a slot of the eye mask in another configuration of the present disclosure.

In present configuration shown in FIG. 4, each one of the slots 114 is straight, but it is not limited thereto. As shown in FIG. 6, the slot 114A may be curved, and as shown in FIG. 7, the slot 114B may be undulating or wavy, such that the speaker assemblies 20 can be adjust and moved along the slot 114A or slot 114B in two directions.

Please refer to FIG. 1 to FIG. 3 again. The second headband 12 is configured to be detachably mounted on the first headband 11 and configured to contact a user's skin. A length of the first headband 11 is larger than a length from an ear to another ear along a circumference of the user's head. A length of the second headband 12 is larger than the circumference of the user's head, such that when the two ends of the second headband 12 are secured on each other and the second headband 12 forms a loop, the head may be enveloped in the second headband 12. In an example, the two ends each includes a mating adhesives or fasteners like a hook-and-loop fastener, commonly referred to as VEL-CRO. Each end can includes a corresponding fastener strip that can be attached via any attachment means like glue, sowing, or otherwise.

The two eye cups 13 are detachably mounted on the second headband 12 and configured to cover the user's eyes respectively. The detachability allows for customized positioning which adds to the comfort and individualization of each mask. Therefore, the second headband 12 is located between the eye cups 13 and the first headband 11. The eye cups 13 can also include a fastener feature to detachably attach to the second headband 12.

Figure 8:
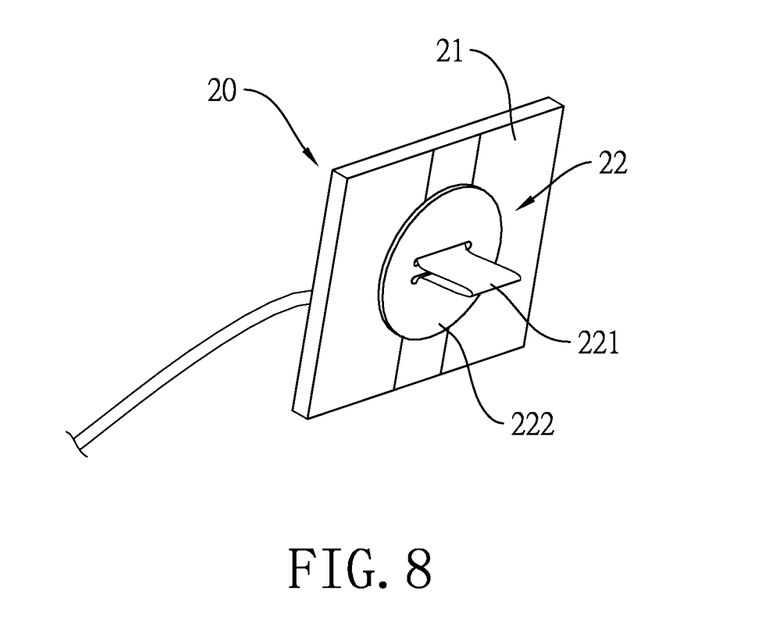
FIG. 8 is an enlarged view of a speaker assemblies of the eye mask in FIG. 1.
Figure 9:
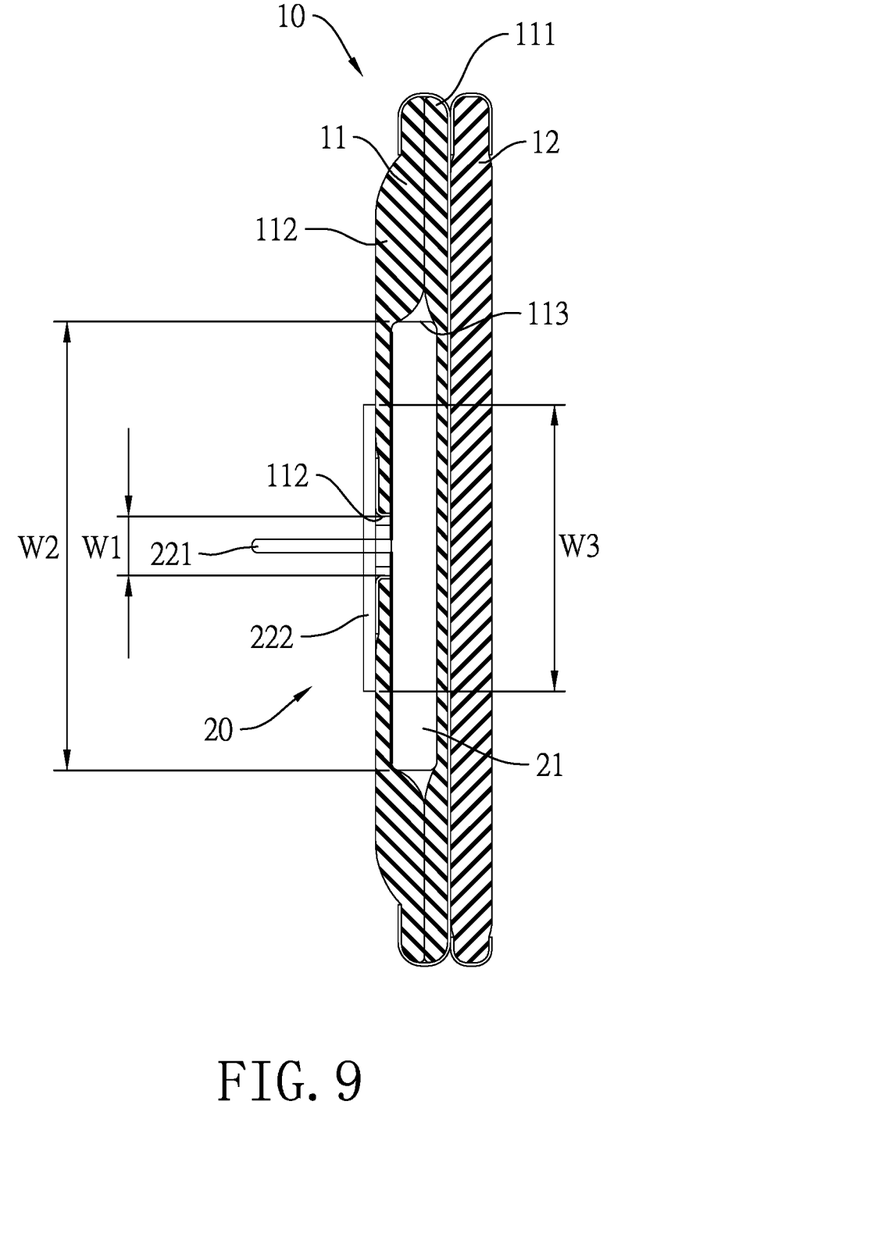
FIG. 9 is a sectional view of an inner space and a speaker assembly of the eye mask in FIG. 1.

Please refer to FIG. 4, FIG. 8, and FIG. 9. The two speaker assemblies 20 are provided in the inner spaces 113 respectively. At least one of the speaker assemblies 20 is configured to be manually moved or adjusted within the corresponding inner space 113. In an example, one of the speaker assemblies 20 is adjustable in location, but the other one may not.

The speaker assemblies 20 can be configured to be coupled to a hidden control unit 40 having multiple button 41, e.g. a power-on button, connect button, and volume control buttons. The speaker assemblies 20 can be coupled to the control unit 40 which is coupled to a power supply like a battery in the control unit 40. In this example, the power supply is a rechargeable battery that further includes an effectively concealed charging port 42. The speaker assemblies 20 are further coupled to the control unit 40 through hidden wires concealed within the main body of the first headband 11. It is further noted that the control unit 40 and/or the speaker assemblies 20 are wirelessly accessible to allow the playing of sound or music from a wireless source like a music or noise app of a smartphone, tablet or otherwise. A wireless communication protocol or module can be incorporated into the control unit 40 to allow for BLUETOOTH compatibility or otherwise In an example, in use, the user may adjust the entire eye mask so that the speaker assembly 20 that cannot be adjusted and aligned with one ear, and then adjust the movable speaker assembly 20 with respect to the entire eye mask to align with the other ear. In another embodiment, the two speaker assemblies 20 are movable and adjustable within the corresponding inner spaces 113.

In a further example, the speaker assemblies 20 each includes a speaker 21 and an operation unit 22. The speaker 21 is configured to be loose or floating within the pocket formed by inner space 113 and movably positioned within one of the inner spaces 113 of the mask main body 10. A general size of the speaker 21 is larger than that of the at least one slot 114, such that the speaker 21 may not easily be moved from or unintentionally fall out of the inner space 113. Precisely, a width W2 of the speaker 2 is larger than the width W1 of the at least one of the slot 114.

The operation unit 22 is located out of the mask main body 10 and connected to the speaker 21 via the at least one slot 114, which allows the user to manually adjust or manipulate the operation unit 22 to slide or move the connected speaker 21. In this embodiment, the operation unit 22 includes a tab 221 and selectively has a positioning piece 222. The tab 221 has two ends. One of the ends of the tab 221 is connected to the speaker 21 and the other end extends out from the slot 114. The positioning piece 222 is mounted on the tab 221 and located between the two ends of the tab 221. A width W3 of the positioning piece 222 is larger than the width W1 of the at least one of the slot 114.

With the aforementioned structures, the eye mask of the present disclosure is capable of not only shading light but also substantially reducing or blocking noise. When wearing the present eye mask, the user may cover the eyes and connect and tie two ends of the second headband 12, thereby securing the eye mask on the head. The eye mask also substantially covers the user's ears. Then, the two speaker assemblies 20 may be moved or adjusted along the two slots 114 of the first headband 11 so that the two speaker assemblies 20 can align with the user's ears respectively. As a result, when the user desires some assistance to fall asleep, the two speaker assemblies 20 can provide a desired sound, music, or white noise to the user's ears, which can reduce or substantially blocks surrounding or environment noise and thus helps the user to sleep.

Even though numerous characteristics and advantages of the present disclosure have been set forth in the foregoing description, together with details of the structure and features of the disclosure, the disclosure is illustrative only. Changes may be made in the details, especially in matters of shape, size, and arrangement of parts within the principles of the disclosure to the full extent indicated by the broad general meaning of the terms in which the appended claims are expressed.

What is claimed is:

1. An eye mask with movable speakers comprising:
   a mask main body configured to cover a user's eyes and ears; the mask main body including:
   at least one inner space corresponding to the user's ears in location; and
   at least one slot formed to allow access to the at least one inner space;
   at least one speaker assembly mounted in the at least one inner space and configured to be adjustable and movable in the at least one inner space; each one of the at least one speaker assembly including:
   a speaker movably positioned in the at least one inner space of the mask main body; and
   an operation unit located out of the mask main body and connected to the speaker via the at least one slot; the operation unit including:
   a tab having two ends, one of the two ends mounted on the speaker and the other end extending out of the at least one slot.

2. The eye mask with movable speakers as claimed in claim 1, wherein:
   a width of the at least one slot is smaller than that of the at least one inner space; and
   a width of the speaker is larger than that of the at least one slot.

3. The eye mask with movable speakers as claimed in claim 2, wherein:
   the operation unit includes:
   a positioning piece mounted on the tab and located between the two ends of the tab, and a width of the positioning piece being larger than that of the at least one slot.

4. The eye mask with movable speakers as claimed in claim 1, wherein the at least one speaker assembly includes two said speaker assemblies, the two speaker assemblies are capable of moving in the at least one inner space.

5. The eye mask with movable speakers as claimed in claim 4, wherein:
the mask main body includes two said slots.

6. The eye mask with movable speakers as claimed in claim 1, wherein each one of the at least one slot is straight, curved, or undulating.

7. The eye mask with movable speakers as claimed in claim 1 further comprising:
a control unit mounted in the mask main body and connected to the at least one speaker assembly, the control unit including multiple buttons.

8. The eye mask with movable speakers as claimed in claim 1, wherein the mask main body includes:
a first headband, the at least one inner space is formed in the first headband;
a second headband detachably mounted on the first headband and configured to contact the user.

9. The eye mask with movable speakers as claimed in claim 8, wherein the mask main body includes:
two eye cups detachably attached on the second headband and configured to cover the user's eyes respectively.

* * * * *